(12) United States Patent
Yim et al.

(10) Patent No.: US 7,995,824 B2
(45) Date of Patent: Aug. 9, 2011

(54) PRECISION SUBTRACTION COMPUTED TOMOGRAPHIC ANGIOGRAPHY

(75) Inventors: Peter J Yim, Belle Mead, NJ (US); John L. Nosher, Basking Ridge, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 174 days.

(21) Appl. No.: 12/221,738

(22) Filed: Aug. 5, 2008

(65) Prior Publication Data

US 2008/0298656 A1    Dec. 4, 2008

Related U.S. Application Data

(63) Continuation-in-part of application No. 11/705,266, filed on Feb. 12, 2007.

(60) Provisional application No. 60/772,478, filed on Feb. 10, 2006.

(51) Int. Cl.
*G06K 9/00*    (2006.01)

(52) U.S. Cl. ...................................................... 382/130
(58) Field of Classification Search .................. 382/128, 382/130, 131, 132
See application file for complete search history.

(56) References Cited

U.S. PATENT DOCUMENTS

5,647,360 A * 7/1997 Bani-Hashemi et al. ..... 600/425
* cited by examiner

*Primary Examiner* — Vu Le
*Assistant Examiner* — Claire Wang
(74) *Attorney, Agent, or Firm* — Barbara V. Maurer (57) ABSTRACT

This invention relates to a novel technique for producing images of arteries that overcomes a significant limitation of conventional computed tomographic angiography (CTA). The technique is performed by the acquisition of pre-contrast computed tomography in addition to the conventional computed tomographic angiography and by the digital subtraction of the pre-contrast computed tomogram from the conventional CTA after alignment of the two images.

1 Claim, 12 Drawing Sheets

PRECISION SUBTRACTION COMPUTED TOMOGRAPHIC ANGIOGRAPHY

This application is a continuation-in part of U.S. Ser. No. 11/705,266, filed Feb. 12, 2007, which application claims priority to U.S. Provisional Application Ser. No. 60/772,478, which was filed on Feb. 10, 2006, the disclosure of which is incorporated herein by reference.

This invention relates to a novel technique for producing images of arteries that overcomes a significant limitation of conventional computed tomographic angiography (CTA). The technique is performed by the acquisition of pre-contrast computed tomography in addition to the conventional computed tomographic angiography and by the digital subtraction of the pre-contrast computed tomogram from the conventional CTA after alignment of the two images.

Arterial stenoses may be obscured by calcified atherosclerotic plaque in computed tomographic angiography (CTA). CTA examination is complicated by the presence of calcified atherosclerotic plaque. When calcification is present, 3D visualization of the arteries using volume rendering is problematic. In the study of Willmann et al, the presence of calcification tended to cause an over-estimation of the degree of stenosis. In their study of 39 consecutive patients with 35 hemodynamically significant stenosis, over-estimation of stenosis occurred in 26 vessel segments. In 20 of the cases in which the stenosis was over-estimated, the primary cause of overestimation of stenosis was the presence of calcification. Ouwendink et al found that wall calcifications in CTA often limited the diagnostic value of CTA and were a statistically significant predictor of when a patient would need additional imaging studies.

Novel approaches have been developed to improve visualization of calcified arteries using CTA. The semitransparent volume-rendering method has shown promise for visualization of vessels in the aortoiliac region with sensitivities and specificities comparable to combined review of the maximum intensity projection and the source cross-sectional images.

Subtraction computed tomographic angiography (sCTA) has been previously developed for suppression of bone and calcification. This process typically involves the registration of the pre-contrast CT and the CTA before digital subtraction of the images. sCTA has more recently been proposed for calcification suppression by Poletti et al. The ability to detect significant stenoses using sCTA was found to be similar to that using digital subtraction angiography (95.9% sensitivity). In this technique, the subtraction was performed after manual registration of the pre-contrast CT and the CTA. In the work of van Straten et al, sCTA was developed specifically for removal of arterial wall calcification using automated registration of pre-contrast CT and CTA and comparing with the results from threshold segmentation of the calcifications. In that study, significant artifacts were found to be present in sCTA when applied to calcified atherosclerotic lesions of the renal artery. Thus there remains a need for improved methods to evaluate atherosclerotic disease.

A simplified technique of subtraction computed tomographic angiography (sCTA) for calcification removal is disclosed herein. In this sCTA method, the examination includes a pre-contrast computed tomogram (pcCT) and a CTA. The pcCT is performed using the CTA scan protocol. Subtraction of the registered pcCT from the CTA is performed after calcifications in the pcCT are registered to the CTA using a piecewise-rigid transformation model. The registration is based on a maximum-cancellation cost-function. Points at the boundary of the artery in the CTA are given a greater weight in the cost function than those towards the center of the artery. sCTA was evaluated using a calcified-artery phantom whose dimensions approximate those of the superficial femoral artery. The phantom represented both calcified plaque surrounding stenotic segments of the artery. pcCT and CTA's were obtained on a 4-multidetector-row CT system with 1.25-mm slice thickness and 0.7-mm in-plane resolution. The phantom was slightly displaced between the pcCT and the CTA. sCTA closely resembled a gold-standard image of the phantom that was obtained with the calcification material removed. The sCTA accurately demonstrated the degree of stenosis and artifacts in the sCTA were minimal. This study demonstrates in that sCTA is feasible.

The goal of the work presented here is to develop and evaluate a novel methodology for sCTA for suppression of calcification.

The present invention relates to the development and validation of a semi-automated methodology for obtaining sCTA as has previously been shown to be possible for removal of bone from CTA.

In the method of the instant invention a novel method for suppression of calcification in CTA by subtraction of pre-contrast CT has been developed and validated. The core of the technique is a registration algorithm that is optimized for precision. Precision is obtained with this algorithm using high-order interpolation, fine-scale increments of translation and rotation and restriction of the registration region to the immediate vicinity of the calcifications. The algorithm was also designed to avoid gross registration error by including user interaction and by using an exhaustive search strategy at scale of the registration within relatively large bounds from the initialization of the registration.

Registration of pcCT and CTA is challenging, in part, because the most significant feature of the CTA, the enhancing lumen, is entirely absent from the pcCT. However, the use of the maximum-cancellation cost function, has been found to be appropriate for registration of these images. Alternative cost functions that were considered and were found to be inappropriate were cross-correlation and least-squares error.

The results of sCTA in the phantom, the observer study, and the clinical study are encouraging. Several variations in the registration algorithm were evaluated in the phantom study. The study showed that high-order interpolation of the images using the windowed-sinc function is necessary to avoid a ripple artifact. The study also showed that the registration cost function should include a scale factor related to the distance transform of the CTA thresholded at 100 Hounsfield units. This scale factor compensates, in part, for the tendency for the calcification region in the pcCT, that is asymmetrically distributed in the cross-sectional view to be registered to a position in the CTA that may be more central to the lumen cross-section than it should be leading to a halo artifact in the sCTA.

The observer study based on the calcified-artery phantom shows clearly that sCTA can potentially be interpreted in a more accurate manner than CTA, even in the cross-sectional view. Of course, an important benefit of sCTA is that it would allow for interpretation in the MIP or other volumetric view in which interpretation can be done faster and with less expertise than for the cross-sectional view. The finding in the observer study of over-estimation of stenosis with CTA of calcified arteries is consistent with the finding in the clinical study of Willmann et al. While the results of the observer study show statistically significant differences between the accuracy of the simulated CTA and the simulated sCTA, the results should be considered as preliminary since the study only involved two stenotic segments. The clinical study demonstrated that realistic-appearing images of vessels can be obtained with sCTA in highly calcified arteries that can be rendered in the MIP.

The proposed algorithm for registration of the pre-contrast CT and the CTA is highly optimized for suppression of calcification. In this algorithm, the focus of registration is only on aligning of corresponding calcifications in the two images. Given the importance of aligning the calcifications, the inclusion of larger regions beyond the calcifications only tends to diminish the accuracy of the alignment of the calcifications. Thus, an all-inclusive image registration, as proposed by Bani-Hashemi et al is likely to have reduced accuracy for calcification suppression. Also, the Maximum-Cancellation cost function, as described above, allows for registration of two images in which a significant feature is entirely absent from one of the images. The Best-Match-Criterion[9] was designed for similar registration conditions and could likely be adapted for use in sCTA for calcification suppression although the comparative advantages of the Maximum-Cancellation and the Best-Match-Criterion cost functions are not yet known.

Significant artifacts in sCTA were observed by van Straten et al that were not observed in our studies. The reason for differences in the results between of van Straten et al and our own are not clear but may be related to related to the use of different models and generations of the CT systems used, differences in the vascular territories in which the technique was evaluated, and to differences in the image registration algorithm. In the image registration, in particular, one notable difference in the methodologies is van Straten et al's use of the least-squares cost function whereas our technique uses a maximum-cancellation cost function. The technique of van Straten et al also uses a technique for correction of misalignment that may result from blurring of the image related to the finite point-spread-function of the CT system. The value technique for correction of misregistration due to image blurring was demonstrated in the phantom study of van Straten et al. However, in our experience, the least-squares cost function is inferior to the maximum-cancellation cost function for sCTA, although this has not been demonstrated in a systematic way. Also, there are significant differences in the search strategy that is used to determine the optimal image registration. In the method of van Straten et al, the optimal registration is found using the downhill-simplex method, whereas a multi-scale method is used in the current work. The multi-scale search strategy is believed to be less sensitive to variation in the initialization of the image registration.

In sum, sCTA using maximum-cancellation registration is a promising technique for the suppression of calcification in CTA. The requirements for user-interaction time and expertise and for computation time are close, if not within, the acceptable limits for adoption for clinical use.

In the method of the instant invention (sCTA method), the examination includes a pre-contrast computed tomogram (pcCT) and a CTA. The pcCT is performed using the CTA scan protocol without the use of contrast media. sCTA is then obtained with the following computational methods.

1. Interpolatation of the pcCT and CTA. The pcCT and the CTA are interpolated by a factor of two in all directions using the windowed sinc method (MIPAV, Center for Information Technology, National Institutes of Health).
2. Segmentation of bone in the interpolated pcCT. The bone is segmented in the pcCT in two steps. First, region growing is performed from a point on the bone identified by the user using a threshold level of 300 Hounsfield units. The region is then dilated in a recursive manner. The bone region at the $n^{th}$ iteration is $B_n$, p, b are points in the image domain, N( ) is the set of 26-neighbors of a given point and f( ) represents the image intensity.

$$p \in B_{n+1} \text{ if } \exists \, b \in B_n \text{ such that } p \in N(b) \text{ and } f(p) < f(b) \quad (1)$$

A maximum of 10 iterations of the dilation are performed. Points in the bone region are set to zero.

3. Registration of pcCT to CTA. The registration is performed using a piecewise-rigid transformation model. In this model, each calcification region in the segmented pcCT is independently registered to the interpolated CTA with rigid transformations. The calcification regions are manually identified then segmented by region-growing of the interpolated pcCT with an threshold intensity of 100 Hounsfield units. Registration is performed in a course-to-fine manner. An exhaustive search is performed of the transformation domain at each scale. At the course scale, the domain of translations is {−1.6 mm, −0.8 mm, 0 mm, 0.8 mm, 1.6 mm} in each direction and the domain of the rotations is {−5°, −4°, −3°, −2°, −1°, 0°, 1°, 2°, 3°, 4°, 5°} around each axis. The registration is performed at successively finer scales of translations. The domains of the translations are as follows:

{−0.8 mm, −0.4 mm, 0 mm, 0.4 mm, 0.8 mm}
{−0.4 mm, −0.2 mm, 0 mm, 0.2 mm, 0.4 mm}
{−0.2 mm, −0.1 mm, 0 mm, 0.1 mm, 0.2 mm}

The registration is based on a maximum cancellation cost-function, C as follows $$C = \sum_{p \in D_I} (d(p) + 5.0) * \text{Truncation}(f(p) - f'(T(p))) \quad (2)$$

$$\text{Truncation}(x) = \begin{cases} x & \text{if } x \geq 0 \\ 0 & \text{if } x < 0 \end{cases}$$

where, f is the image intensity of the interpolated CTA, and f' is the image intensity of the interpolated pcCT. The discrete domain $D_I'$ is the calcification region in the pcCT. T is a rigid transformation. d( ) is the signed distance-transform, in mm, of the CTA at 100 Hounsfield units. This cost-function is maximized to obtain the desired registration.

4. Subtraction. The registered calcification region is then subtracted from the interpolated CTA to obtain the sCTA.
5. Segmentation of bone in the interpolated sCTA. Step 2 is repeated for segmentation of the bone from the sCTA.

2.2 Phantom Study sCTA was studied using a phantom resembling a calcified arterial segment on computed tomography. The phantom was constructed from a drinking straw on which two stenotic segments were imposed. The stenoses were created by stretching a segment of the straw after heating the straw with steam. The straw was then mounted in a 2-liter plastic container. The container was filled with water for imaging. The appearance of calcification was created by overlaying modeling clay around the stenotic segments. The modeling clay was overlaid in a melted state so that there was good contact between the clay and the stenotic segment of the straw. The straw was alternately filled with water and corn syrup to obtain the appearance of a calcified arterial segment without and with contrast respectively. Air bubbles were removed from on any surfaces of the artery phantom before the imaging.

CT images of the phantom were acquired with a four-detector row Lightspeed Plus CT (GE Medical Systems). The gold-standard for evaluation of sCTA was a CT image obtained of the phantom before placement of the modeling clay representing the calcification. The CT image was acquired using the "Routine head" protocol with a tube voltage of 140 kvp, a tube current of 255 mA. The images were reconstructed to 1.25-mm slice thickness and 0.34-mm in-plane resolution. The pcCT and CTA images were acquired after placement of the modeling clay representing the calcification. The pcCT and CTA images were acquired using the "Run off" protocol. These images were acquired with a tube voltage 120 kvp and a tube current of 150 mA and were reconstructed to 1.25-mm slice thickness and 0.68 mm in-plane resolution. The phantom was shifted between the acquisition of the pcCT and CTA images.

Patients

This study was based on imaging from two patients who underwent a combined CTA and ncCT study for suspicion of arterial occlusive disease of the lower extremities. Analysis of the images was approved by our institutional review board. Acquisition of the combined CTA and ncCT was performed for clinical considerations in these patients.

Image Acquisition; Clinical Cases

Imaging was performed on a 64-detector-row Lightspeed VCT. The images were acquired with the standard-of-care clinical protocol that includes a tube voltage of 120 kvp and a tube current of 101 mA and were reconstructed at a slice thickness of 1.25 mm and an in-plane resolution of 0.75 mm. Images were acquired with a helical acquisition with a pitch of 1.375. Motion of the subject was not restricted during the CT examination and the subject was not requested to remain motionless between acquisition of the pcCT and the CTA.

Image Registration

Some patient motion is expected to occur between the two phases of the subtraction CTA acquisition, even if the patient is instructed not to move. Thus, in general, a correction must be applied to one of the images to compensate for that motion. A semi-automated co-registration algorithm was used in this study. The algorithm includes manual registration, manual identification of calcifications and computational registration. Details of the registration process are given below.

The first step in the registration process is manual registration of the non-contrast CT and the CTA. Manual registration is expected to be relatively reliable since inter-scan motion will usually be small-scale and primarily translational in nature. Thus corresponding features in the two images can be recognized without extensive searching. Furthermore, the structures that are of most interest are the calcifications that have distinctive small-scale features that can be matched between the two images. Thus, the manual registration process, for a given arterial territory consists of identifying a matching pair of points from the two images on a calcification. One of the images is then shifted both in- and out-of-plane to produce alignment of those matching points.

Figure 9:
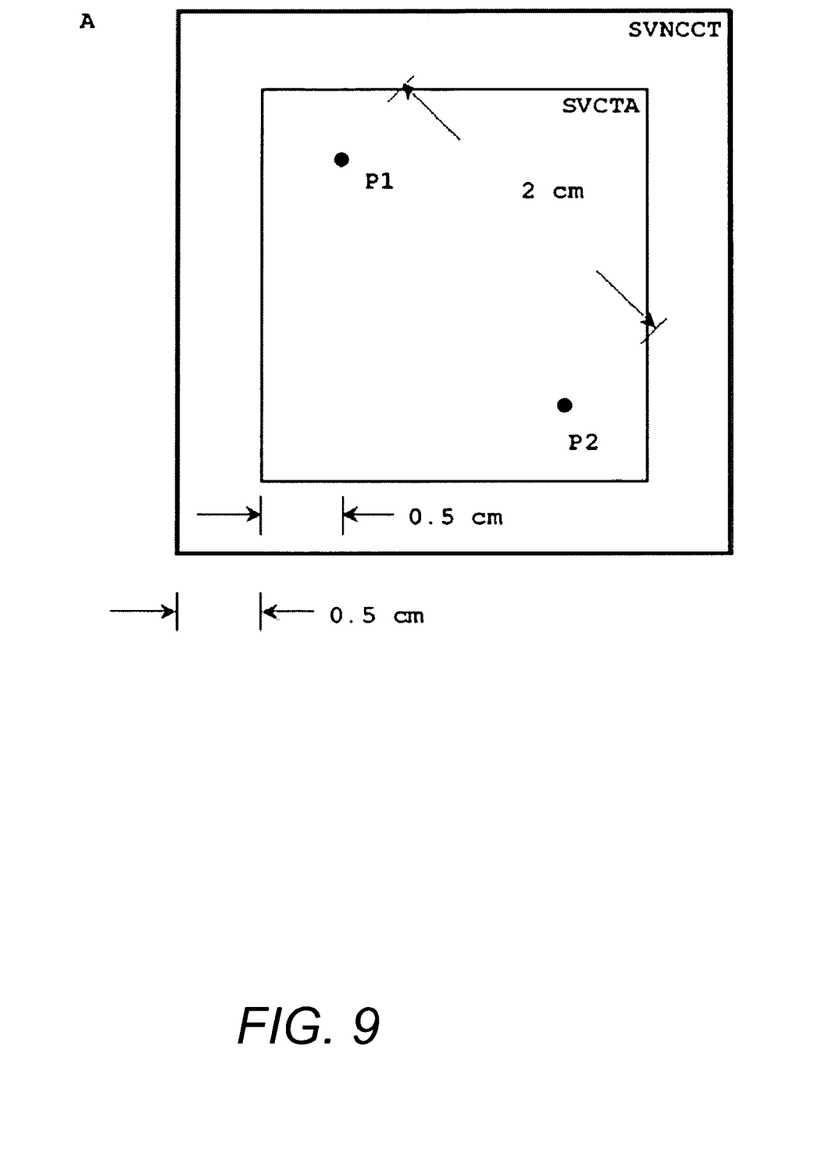
FIG. 9 shows image regions included in co-registration of the non-contrast computed tomography and the computed tomographic angiography. The regions are based on a series of two or more points along the calcified artery identified by the user. A box is then constructed such for a pair of consecutive points (P1, P2) such that those points are located at the diametrically opposite corners. The box is then extended outwards by 0.5 and 1.0 cm to form an image sub-volumes in the computed tomographic angiography (SVCTA) and in the non-contrast CT (SVNCCT).

In the proposed registration algorithm, the entire images are not registered to one another since the spatial transformation or motion correction between the two images may become complex for large volumes of tissue including elastic deformations. Instead, the images are registered to one another in segments with relatively limited volumes. Within such volumes, assumptions of the rigidity of the tissue are valid or nearly so. More specifically, these registration subvolumes are defined to encompass calcifications and ideally are positioned such that the calcifications are centered within the volumes. The accuracy of the subsequent computational registration will depend to some extent on whether there are an adequate number of points within calcification within the sub-volume and on whether those points are sufficiently centered within the sub-volume. These sub-volumes can be obtained in the following manner. First, the user places a series of points along a calcified segment in the artery with each point separated from the previous point by approximately 2 cm. This series of points defines the path of a calcified segment of an artery and also subdivides the artery in the axial direction. Each pair of consecutive points in this series can then be used to define a bounding box that surrounds the vessel and calcifications. First, a box is defined by considering the two points as its diametrically opposed corners. Then, that box is extended outwards by one centimeter in all directions to form the sub-volume bounding box. Thus, the bounding box has a minimum possible dimension of 2 cm in any direction and a maximum dimension of 4 cm. Computational registration is then applied sequentially to each of the sub-volumes within the respective bounding boxes. The process of constructing the sub-volumes for registration is shown schematically in FIG. 9. In our study, all interactive aspects of the registration process were performed in MIPAV (National Institutes of Health) including identifying points for manual registration, identifying points along the calcified vessel axes and cropping of the images.

Corresponding subvolumes of the non-contrast CT and the CTA were then co-registered using the mutual-information algorithm. The software algorithm was implemented in-house in "C" on the IRIS Explorer prototyping platform (Numerical Algorithms Group Ltd, Oxford, UK) on a Windows 2000 workstation. Preprocessing of the sub-volumes included resampling to increase the resolution by a factor of two using a $3^{rd}$ order b-spline function as implemented in MIPAV (National Institutes of Health). Within each CTA sub-volume, a set of points was defined that were expected to be either lumen or calcification. These points were identified by thresholding of the CTA at a level of 100 HU and by manual contouring to exclude possible regions of bone in the sub-volumes. Points within a 0.5-cm margin in the CTA were also excluded from this set to ensure complete overlap with the non-contrast CT for a wide range of translations and rotations. Calculations of mutual information were then based entirely on these lumen/calcification points. The histogram bin size for computing the mutual information cost function was set such that there was an average of one image-lumen/calcification point per bin in the joint histogram. Registration was based on a rigid model of motion with both translational and rotational components. Intra-registration resampling was performed using tri-linear interpolation. In the registration process, the CTA served as the reference image while the non-contrast CT served as the floating image. Optimization was performed using the gradient-descent method with translational increments of 0.1 mm in each direction and rotational increments 0.2° around each axis.

Based on the results of the mutual-information registration, the optimal motion correction was applied to the entire non-contrast CT sub-volume and then was arithmetically subtracted from the CTA sub-volume. The resulting subtraction sub-volume was then re-inserted into its original position in the CTA after cropping a margin of 0.5 cm where subtraction may not have been effective due to non-overlap of the CTA sub-volume and the non-contrast CT sub-volume.

Image Analysis; Vascular Phantom sCTA of the phantom was rendered with the maximum intensity projection (MIP) at a series of views perpendicular to the native slice plane. The views spanned 180° at 30° increments. Image resampling for performing the rotations was done using trilinear interpolation. The orthonormal perspective was used for creating the MIP's. The series of MIP's was then viewed by researcher (PJY) using MIPAV (National Institutes of Health) to select a point of maximal stenosis in one of the views. Lines for forming image-intensity profiles were drawn at the point of maximal stenosis and at a normal segment of the model using the line tool. An edge enhancement filter, the gradient magnitude, was then applied to the MIP using MIPAV. The convolution kernel of the filter was set to a space constant of 1.0×1.0 pixels. Image-intensity profiles of the gradient-magnitude image at the stenotic and normal locations were then analyzed to determine the respective lumenal diameters. Specifically, the diameter was considered to be the distance between the two highest maxima in the image intensity profiles corresponding to the two opposing sides of the lumen. A similar process was used for measuring diameters in the gold-standard images although profiles were obtained from the cross-sectional imaging.

The effect of initialization error on the accuracy of the registration was also evaluated. The initialization position of the floating image was varied by displacements of up to 5.0 mm in each direction from the displacement obtained by registration using a best—guess initialization.

Observer Study

An observer study was carried out to compare the accuracy of subtraction CTA with conventional CTA in the measurement of the stenosis severity. The observers in this study were three licensed, interventional radiologists. The study was performed using images of the calcified-artery phantom described in section 2.2.

The observers measured the degree of stenosis of the two stenotic segments of the calcified-artery phantom using MIPAV software (National Institutes of Health). All measurements were made from axial cross-sectional views. Measurements of vessel segment diameter on the simulated CTA and on the simulated subtraction CTA. Vessel diameter measurements were made after 8× bilinear interpolation of the images. The observers set the image contrast using either the Quick-LUT tool, that automatically sets the contrast based on a region of interest that is drawn by the user, or using the Adjust-Window-and-Level tool. Length measurements were made with the Draw-Line-VOI tool. The observers were blinded to gold-standard measurements of the vessel diameter, did not see the actual phantom or know of the details of the construction of the phantom.

Gold-standard measurements of vessel diameter were made in the following manner. The gold-standard CT of the phantom was 4× bilinearly interpolated. The gradient magnitude of the image was then obtained by convolution with 2D kernel using MIPAV. The scale of the Gaussian associated with the convolution kernel was 1.0 pixels. An intensity profile was then obtained in a normal segment and in the stenotic segments at the location that was judged to have maximal narrowing and at the orientation that was judged to have the minimal diameter. The edge of the lumen was considered to be the point at which the gradient magnitude was maximal and the diameter of the vessel segment was determined by finding the distance between the maxima in the intensity profile associated with opposing sides of the vessel segment.

2.4 Clinical Study

A. sCTA examination was obtained in one subject with peripheral arterial occlusive disease. Imaging was performed on a 64-detector-row Lightspeed VCT. The images were acquired with a tube voltage of 120 kvp and a tube current of 101 mA and were reconstructed at a slice thickness of 1.25 mm and an in-plane resolution of 0.75 mm. Motion of the subject was not restricted during the CT examination and the subject was not requested to remain motionless between acquisition of the pcCT and the CTA.

B. sCTA of clinical cases was reviewed by two radiology residents (AB,IH), for detection of hemodynamically significant stenoses. Such stenoses were defined as points with greater than or equal to 50% narrowing that could be identified with at least moderate confidence. Rendering of the clinical sCTA was performed in a similar manner as for the phantom study. Rendering sCTA was performed after removal of bone using manual contouring.

Twelve (12) calcified arterial segments were included in the analysis from the superficial femoral artery (3), popliteal artery (2) and popliteal trifurcation arteries (7). The total length of calcified segments of arteries included in the study was approximately 28 cm. The image co-registration and subtraction was performed for fourteen (14) 2-cm calcification sub-volumes.

3. Results

Figure 1:
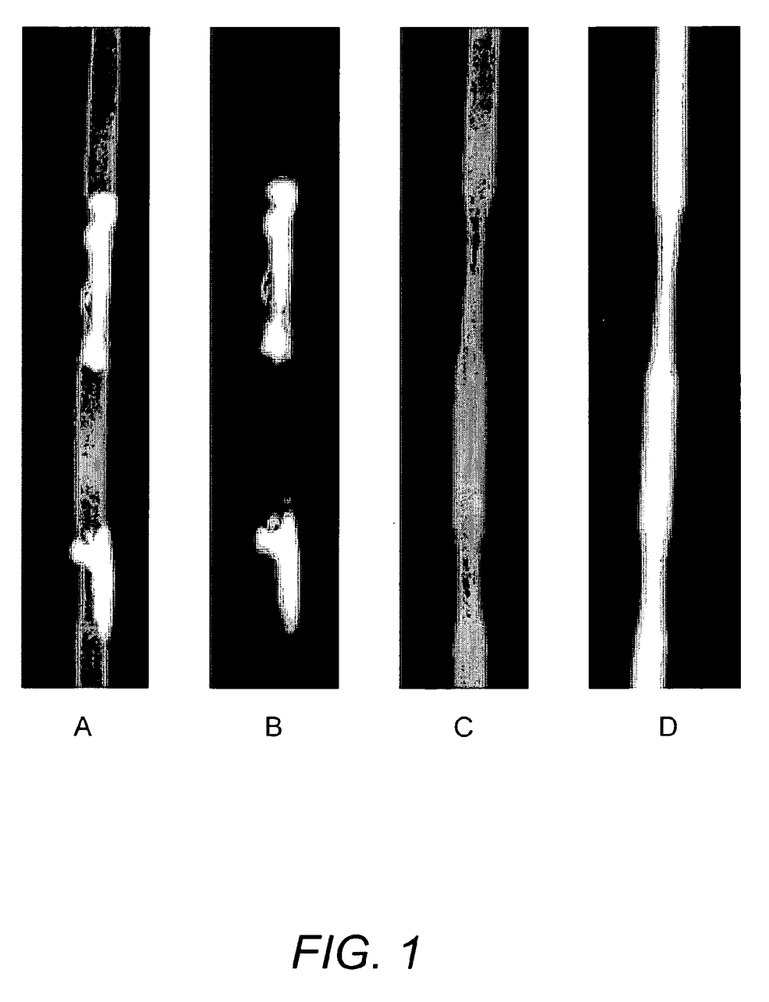
FIG. 1 shows an sCTA phantom study. Maximum intensity project (MIP) is shown of CTA of calcified-artery phantom (a), of pcCT of phantom (b), of sCTA of phantom (c) and of gold standard CTA which was obtained before the placement of the clay that represented the calcification.
Figure 2:
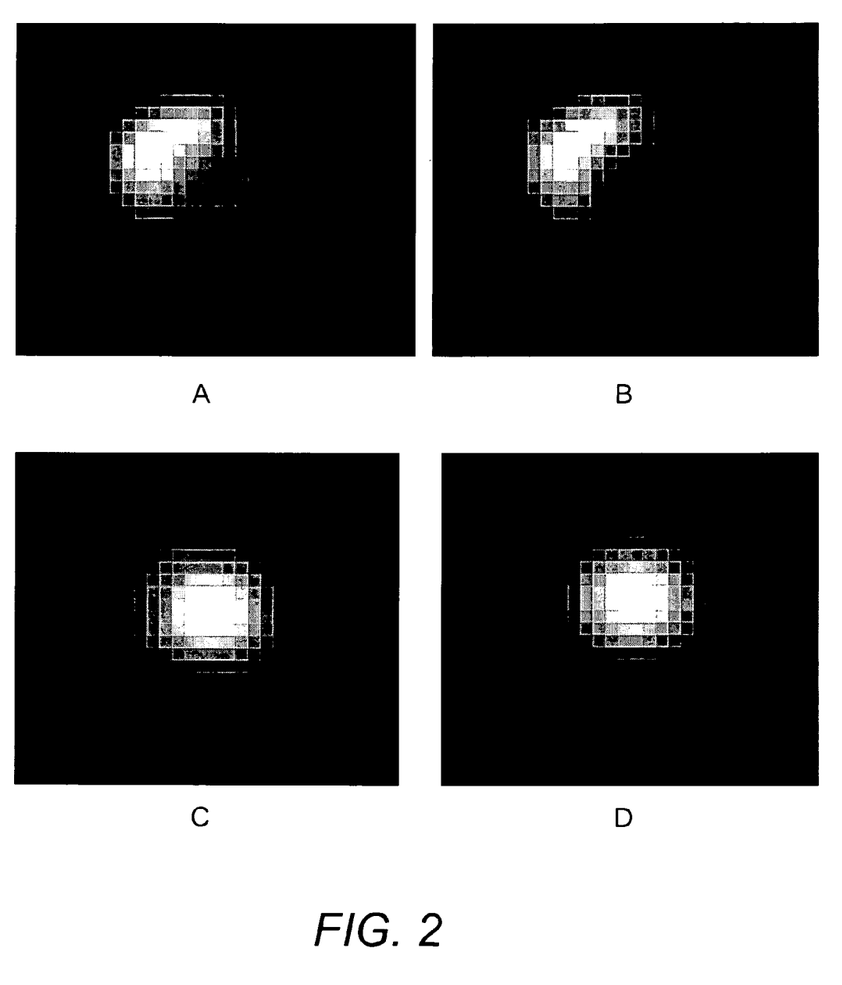
FIG. 2 shows a cross-sectional view of phantom. Cross-sections of phantom are shown at the same location in CTA (a), in pcCT (b), in sCTA (c) and in the gold-standard CTA (d).
Figure 3:
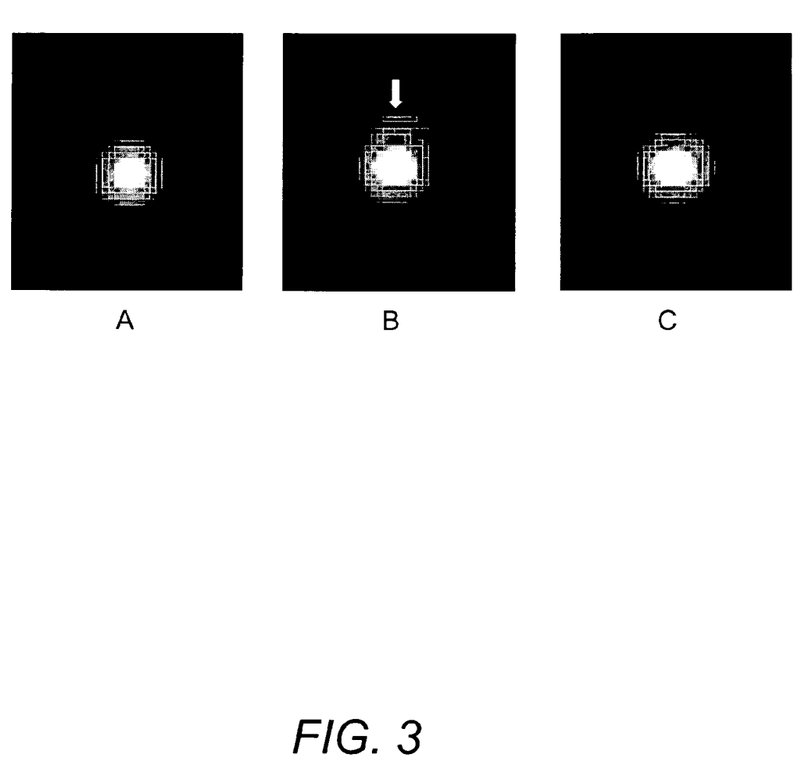
FIG. 3 shows a comparison of trilinear and windowed-sinc interpolation. A ripple artifact (arrow) is seen in the sCTA using trilinear interpolation (b). This artifact is minimal when using the windowed-sinc interpolation (c). The gold-standard CTA for the same location as the sCTA is shown in (a).
Figure 4:
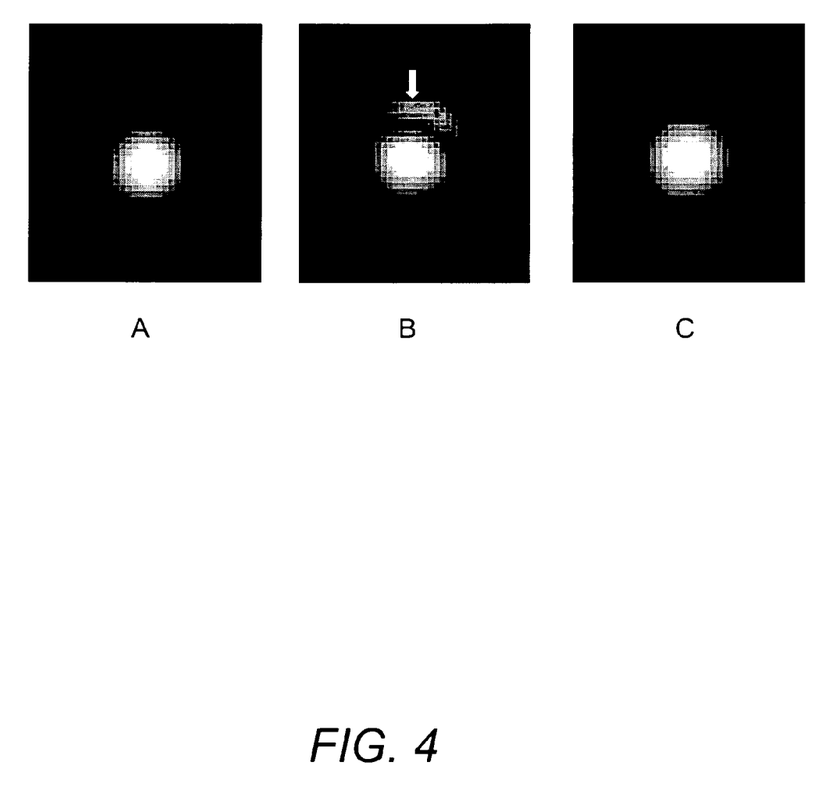
FIG. 4 shows a comparison of sCTA with and without weighting of the cost function based on the distance function representing the distance to the boundary of the vessel. A halo artifact (arrow) is seen in the sCTA without weighting based on the distance function (b). This artifact is minimal when using weighting based on the distance function (c). The gold-standard CTA for the same location as the sCTA is shown in (a).

3.1 Phantom Study sCTA of the calcified-artery phantom is similar in appearance to the gold-standard CTA as shown in FIGS. 1 and 2. The use of trilinear interpolation for performing registration of the pcCT with the CTA was found to produce a ripple artifact as shown in FIG. 3. This artifact was reduced by the use of windowed-sinc interpolation. sCTA can have a halo artifact using a registration cost-function that is not weighted by the distance transform of the CTA as shown in FIG. 4. The halo artifact is not present when the registration cost-function is weighted by the distance transform.

3.2 Observer Study

Figure 5:
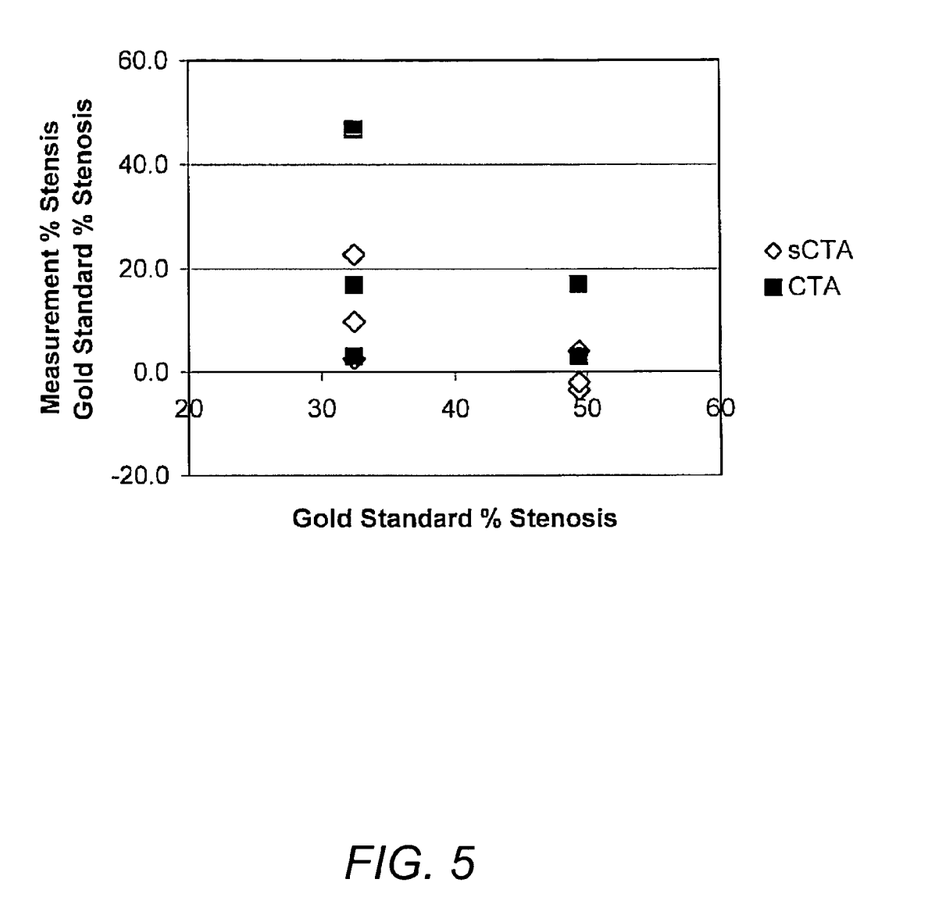
FIG. 5 shows a Bland-Altman plot of measurement of stenosis by CTA and sCTA for observer study of calcified-artery phantom. Smaller error in the measurement of stenosis was found for sCTA than for CTA.

Stenosis severity in the phantom vessel segments was overestimated by the simulated CTA with respect to the gold-standard measurement by 17±24%. In a paired, two-tailed comparison, using the t-test, the difference in the measurement of the stenosis by the simulated CTA from the gold-standard measurement was statistically significant (p=0.05). The measurement of stenosis by the simulated subtraction CTA was not statistically different from the gold-standard measurement (p=0.32). The absolute magnitude of the error in the measurement of stenosis with the simulated CTA was greater than that for the simulated subtraction CTA in a paired, two-tailed t-test (p=0.02). Comparison of measurements of stenosis by CTA and sCTA with gold-standard measurements is shown in a Bland-Altman plot in FIG. 5.

Figure 6:
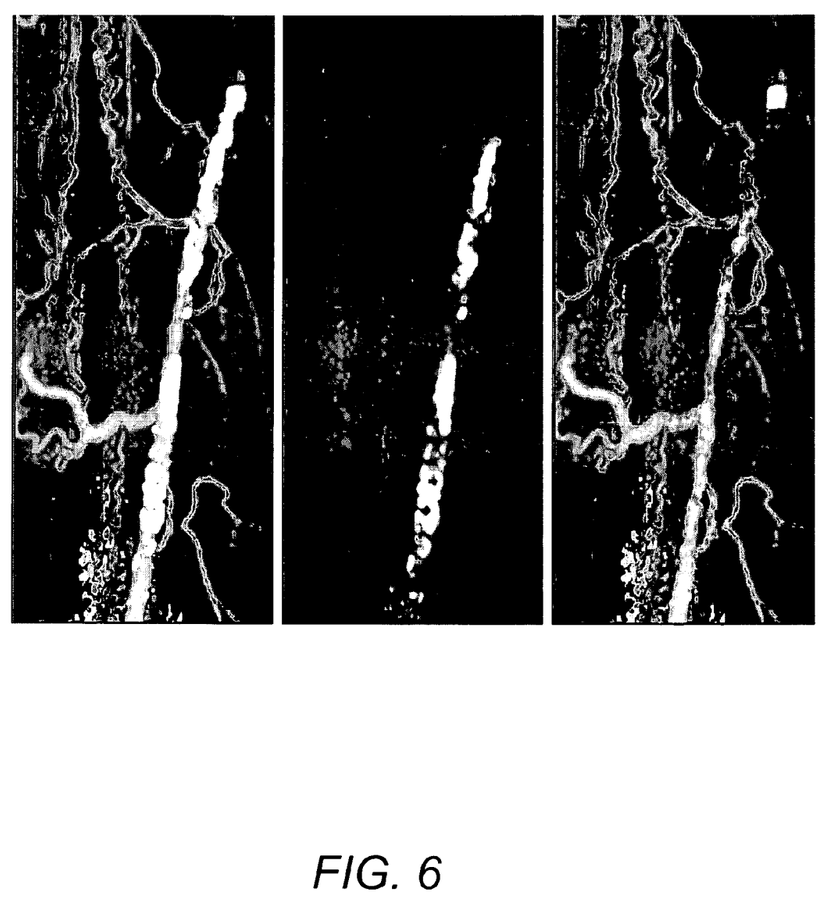
FIG. 6 shows an sCTA of the superficial femoral artery (SFA). The SFA is shown as a MIP in the CTA (a), in the pcCT (b) and in the sCTA (c).
Figure 7:
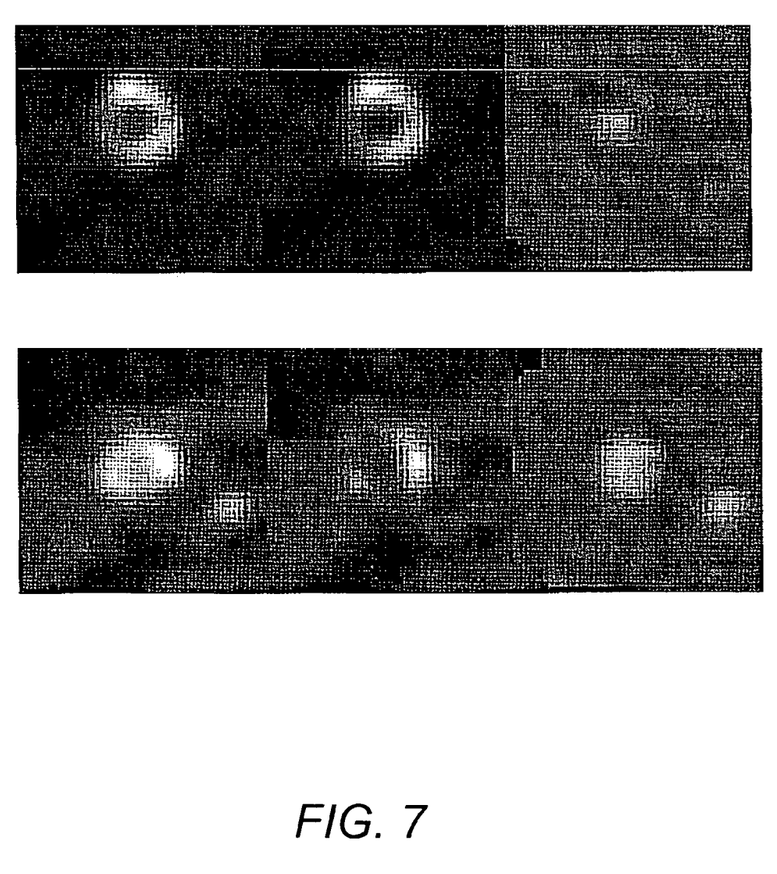
FIG. 7 shows a comparison of CTA, pcCT and sCTA in cross-sectional images. Top row shows region of moderate stenosis in axial cross section at upper level indicated in FIG. 5(a) for CTA (left), pcCT (center), and sCTA (right). Bottom row shows same comparison in region of mild stenosis for cross sections at lower level indicated in FIG. 5(a).
Figure 8:
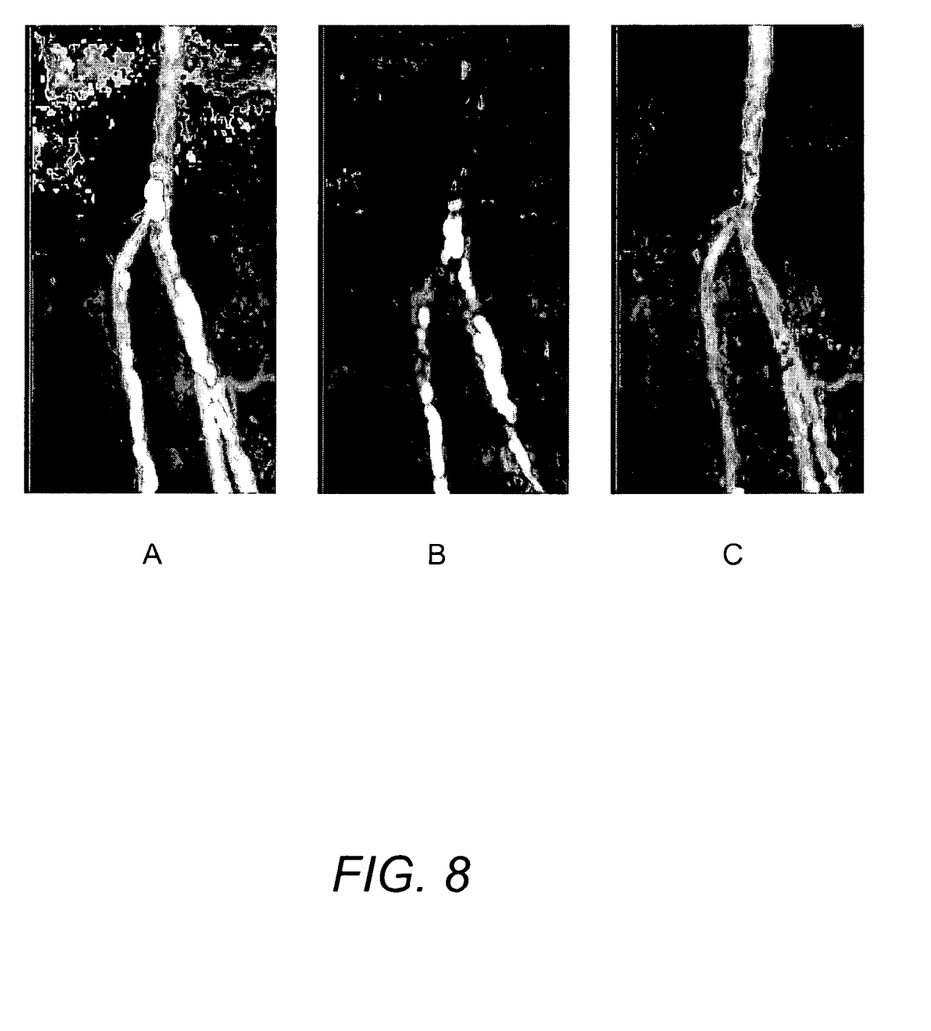
FIG. 8 shows an sCTA of the politeal trifurcation. The popliteal trifurcation is shown as a MIP in the CTA (a), in the pcCT (b) and in the sCTA (c).

3.3 Clinical Study sCTA produced realistic results for the territory of the superficial femoral artery and the popliteal trifurcation as shown in FIGS. 6 and 8 respectively. A comparison of the CTA, pcCT and sCTA is shown in FIG. 7 in the axial cross-sectional view for mild and moderately stenotic segments of the vessel. sCTA required approximately 15 minutes for processing of each vascular territory.

3.4 Additional Discussion

Figure 10:
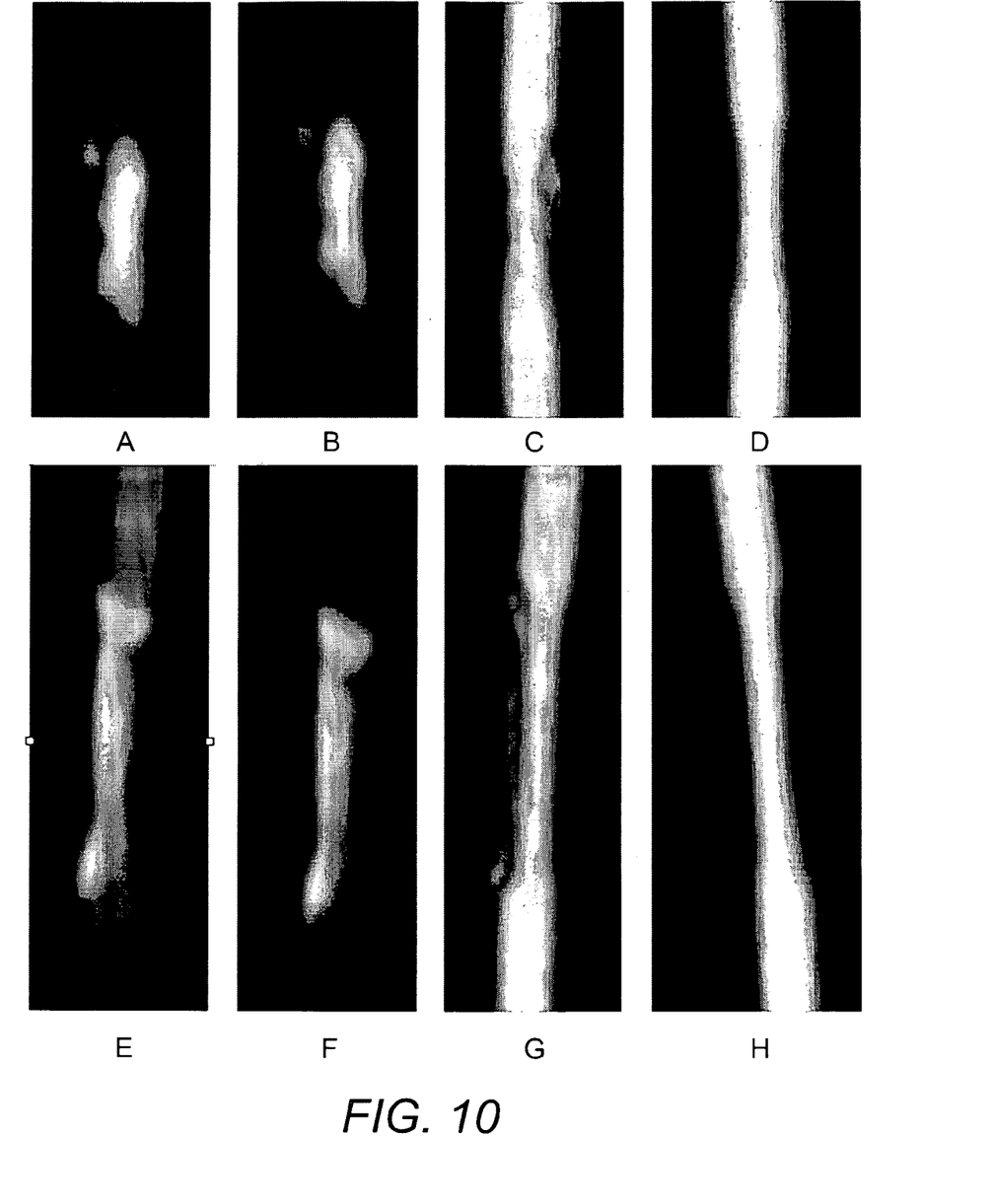
FIG. 10 shows subtraction computed tomographic angiography of calcified-artery phantom. The images represent the results of simulation of the computed tomographic angiography (a,e), the non-contrast computed tomography (b,f) and the subtraction computed tomographic angiography (c,g). Reference images (d,h) were obtained from imaging of the phantom without calcification material present.
Figure 11:
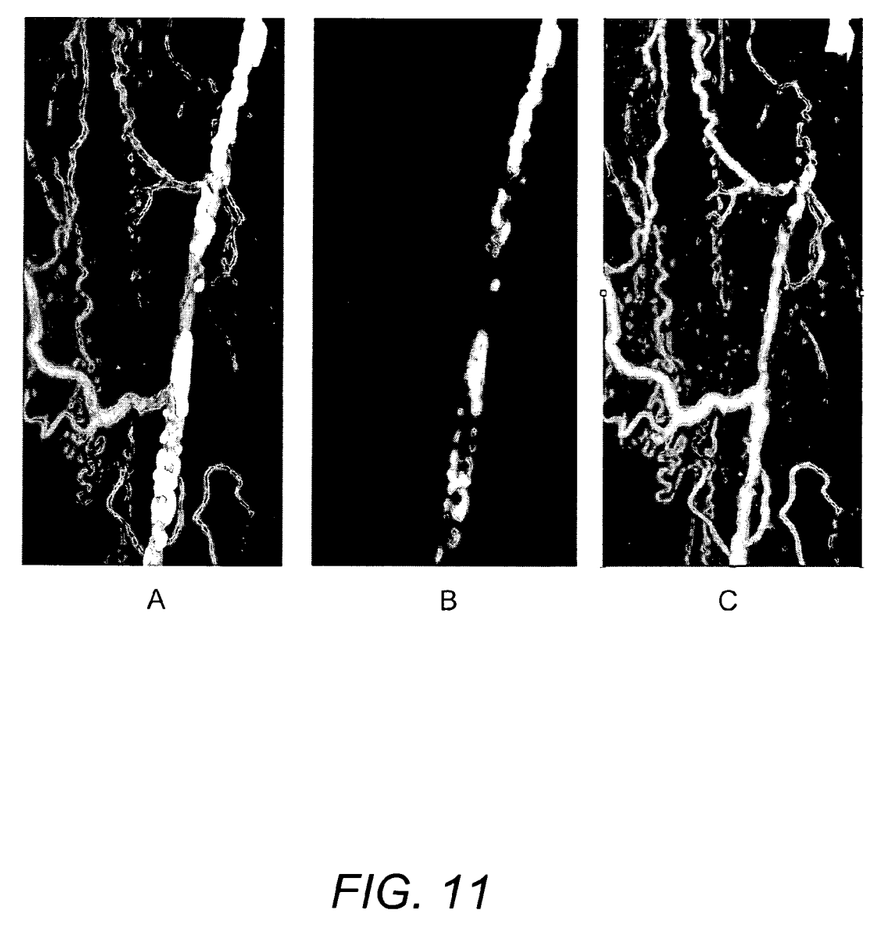
FIG. 11 shows the effect of transformation error in the initialization of the image registration on the accuracy of the image transformation following registration. Only the translational component of the image transformation is represented in the error. The true image transformation was estimated as that obtained from a best-guess initialization followed by MI registration.
Figure 12:
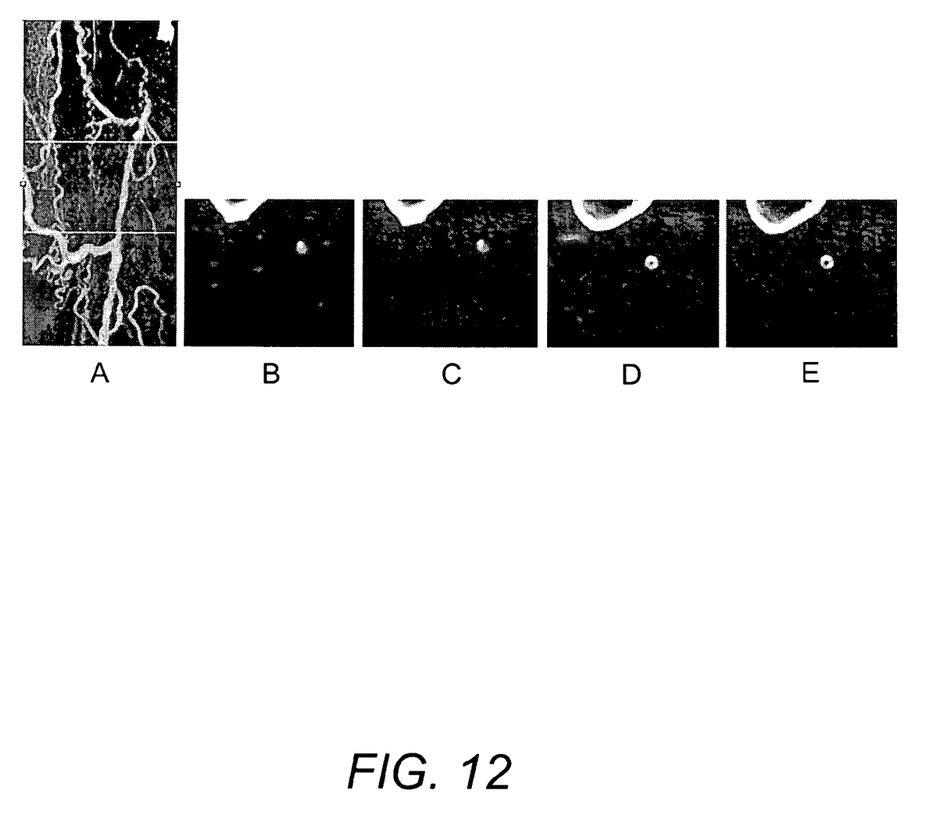
FIG. 12 shows the subtraction computed tomographic angiography in the territory of the superficial femoral artery. Subtraction computed tomographic angiography (c) obtained from computed tomographic angiography (a) and non-contrast computed tomography (b).

A high degree of suppression of the calcification component was achieved in the phantom study as is shown in FIG. 10. Residual artifact from the calcification was seen but was significantly lower in intensity than the lumen and did not obstruct the view of the lumen in the MIP. Measurement of the degree of stenosis from the sCTA was within 8±4% for the two models. The registration process was found to be insensitive to the initialization for error in the initialization position of up to 2.0 mm. Significant registration error was found to occur for larger initialization errors as is shown in FIG. 11.

sCTA was considered to be technically successful in all 14, 2-cm calcifications, as judged (by PJY) to produce an arterial segment with a realistic appearance. An example of sCTA is shown in FIG. 12. A high degree of inter-observer agreement was also obtained for the detection of hemodynamically significant stenoses (K=0.86). A breakdown of the outcome combinations is shown in Table 1 wherein "Positive" indicates number of arterial segments in which stenosis was detected, "Negative" indicates number of arterial segments in which stenoses was not detected.

TABLE 1

|  | Negative | Positive | Total |
|---|---|---|---|
| Negative | 6 | 0 | 6 |
| Positive | 1 | 5 | 6 |
| Total | 7 | 5 | 12 segments |

Practical aspects of the clinical use of sCTA include the degree of user interaction and computation time. The use of this implementation of sCTA was found to require modest user inter-action that primarily relates to the identification of corresponding points in the ncCT and the CTA for performing manual registration. Identification of such points was not found to be problematic in the cases included in this study. The identification of one point within a given vascular territory was found to be adequate. Manual registration had to be repeated in one of the three vascular territories when obvious mis-registration was seen in the sCTA. The computation time for performing sCTA was approximately nine seconds for each 2-cm calcification including eight seconds for image interpolation for each 2-cm calcification and 1 second for MI image co-registration.

REFERENCES

1. Willmann J K, Baumert B, Schertler T, Wildermuth S, Pfammatter T, Verdun F R, Seifert B, Marincek B, Bohm T., "Aortoiliac and lower extremity arteries assessed with 16-detector row CT angiography: prospective comparison with digital subtraction angiography," Radiology. 2005 September; 236(3):1083-93.
2. Ouwendijk R, Kock M C, van Dijk L C, van Sambeek M R, Stijnen T, Hunink M G, "Vessel wall calcifications at multi-detector row CT angiography in patients with peripheral arterial disease: effect on clinical utility and clinical predictors," Radiology. 2006 November; 241(2):603-8.
3. Portugaller H R, Schoellnast H, Tauss J, Tiesenhausen K, Hausegger K A. "Semitransparent volume-rendering CT angiography for lesion display in aortoiliac arteriosclerotic disease," J Vasc Interv Radiol. 2003 August; 14(8):1023-30.
4. Rollano-Hijarrubia E., van der Meer F., van der Lugt A, Weinans H, Vrooman H, Vossepoel A, Stokking R, "Improving the imaging of calcifications in CT by histogram-based selective deblurring," Medical Imaging 2005: Physics of Medical Imaging. Edited by Flynn, Michael J. Proceedings of the SPIE, Volume 5745, pp. 67-78 (2005).

5. Flohr T G, McCollough C H, Bruder H, Petersilka M, Gruber K, Suss C, Grasruck M, Stierstorfer K, Krauss B, Raupach R, Primak A N, Kuttner A, Achenbach S, Becker C, Kopp A, Ohnesorge B M, "First performance evaluation of a dual-source CT (DSCT) system," Eur Radiol. 2006 February; 16(2):256-68.
6. Boll D T, Hoffmann M H, Huber N, Bossert A S, Aschoff A J, Fleiter T R. "Spectral coronary multidetector computed tomography angiography: dual benefit by facilitating plaque characterization and enhancing lumen depiction," J Comput Assist Tomogr. 2006 September-October; 30(5): 804-11.
7. Bani-Hasemi A, Krishnan A, Samaddar S, "Warped matching for digital subtraction of CT-angiography studies", Proc. SPIE Vol. 2710, p. 428-437, Medical Imaging 1996.
8. S. M. Kwon, Y. S. Kim, T. Kim, J. B. Ra, "Novel digital subtraction CT angiography based on 3D registration and refinement," SPIE Medical Imaging 2004, Volume 5370, p. 1156-1165.
9. Beier J, Oellinger H, Richter C S, Fleck E, Felix R. "Registered image subtraction for CT-, MR- and coronary angiography," Eur Radiol. 1997; 7(1):82-9.
10. van Straten M, Venema H W, Streekstra G J, Majoie C B, den Heeten G J, Grimbergen C A, "Removal of bone in CT angiography of the cervical arteries by piecewise matched mask bone elimination," Med Phys. 2004 October; 31(10): 2924-33.
11. Poletti P A, Rosset A, Didier D, Bachmann P, Verdun F R, Rutschmann O, Vallee J P, Terrier F, Khatchatourov G., "Subtraction CT angiography of the lower limbs: a new technique for the evaluation of acute arterial occlusion," AJR Am J. Roentgenol. 2004 November; 183(5): 1445-8.
13. Rutten A, Isgum I, Prokop M., "Coronary Calcification: Effect of Small Variation of Scan Starting Position on Agatston, Volume, and Mass Scores," Radiology. 2007 Nov. 16; [Epub ahead of print]
14. Suzuki M, Ozaki Y, Komura S, Nakanishi A., "Intracranial carotid calcification on CT images as an indicator of atheromatous plaque: analysis of high-resolution CTA images using a 64-multidetector scanner," Radiat Med. 2007 October; 25(8):378-85. Epub 2007 Oct. 26.
14. Maldonado T S, "What are Current Preprocedure Imaging Requirements for Carotid Artery Stenting and Carotid Endarterectomy: Have Magnetic Resonance Angiography and Computed Tomographic Angiography Made a Difference?," Semin Vasc Surg. 2007 December; 20(4):205-15.
15. Pluim J P, Maintz J B, Viergever M A., "Mutual-information-based registration of medical images: a survey," IEEE Trans Med Imaging. 2003 August; 22(8):986-1004.
16. Loeckx D, Drisis S, Maes F, Vandermeulen D, Marchal G, Suetens P, "Removal of Plaque and Stent Artifacts in Subtraction CT Angiography Using Nonrigid Registration and a Volume Penalty", Conf Proc IEEE Eng Med Biol Soc. 2005; 4:4294-7
17. Vogel W V, Schinagl D A, Van Dalen J A, Kaanders J H, Oyen W J, "Validated image fusion of dedicated PET and CT for external beam radiation therapy in the head and neck area," Q J Nucl Med Mol Imaging. 2007 Mar. 25; [Epub ahead of print]
18. Ali R. Bani-Hashemi, Arun Krishnan, and Sumitro Samaddar, "Warped matching for digital subtraction of CT-angiography studies," Proceedings of SPIE—Volume 2710, Medical Imaging 1996: Image Processing, Murray H. Loew, Kenneth M. Hanson, Editors, April 1996, pp. 428-437
19. Yim, Peter J.; Nosher, John L., "Subtraction computed tomographic angiography: use of pre-contrast images for calcification removal," Medical Imaging 2006: Physiology, Function, and Structure from Medical Images. Edited by Manduca, Armando; Amini, Amir A. Proceedings of the SPIE, Volume 6143, pp. 805-811 (2006).
20. van Straten M, Venema H W, Streekstra G J, Reekers J A, den Heeten G J, Grimbergen C A., "Removal of arterial wall calcifications in CT angiography by local subtraction," Med Phys. 2003 May; 30(5):761-70.

The invention claimed is:

1. A method for the suppression of calcification in computed tomographic angigraphy (CTA) which comprises:
    a. performing a pre-contrast computed tomogram (pcCT);
    b. performing a CTA; and
    c. computing a digital subtraction computed tomographic angiogram (sCTA) by:
        i. interpolating the pcCT and the CTA by a factor of two in all directions using the windowed sinc method;
        ii. segmenting the bone in the interpolated pcCT;
        iii. registering each calcification region in the segmented pcCT to the interpolated CTA with piecewise rigid transformation; and
        iv. subtracting the registered calcification region from the interpolated CTA; and
    d. displaying the sCTA.

* * * * *